United States Patent [19]

Gabriels, Jr.

[11] Patent Number: 4,996,154

[45] Date of Patent: Feb. 26, 1991

[54] METHOD FOR GROWING CELLULAR TISSUE

[75] Inventor: Joseph E. Gabriels, Jr., Brighton, Mass.

[73] Assignee: Millipore Corporation, Bedford, Mass.

[21] Appl. No.: 347,448

[22] Filed: May 4, 1989

[51] Int. Cl.$^5$ .......................... C12N 5/06; C12N 5/08
[52] U.S. Cl. ...................... 435/240.241; 435/240.23; 435/240.243
[58] Field of Search .................... 435/240.23, 240.241, 435/240.243

[56] References Cited

U.S. PATENT DOCUMENTS

| | | |
|---|---|---|
| 4,016,036 | 4/1977 | Rheinwald et al. . |
| 4,485,096 | 11/1984 | Bell . |
| 4,609,551 | 9/1986 | Caplan et al. ................ 435/240.243 |
| 4,645,669 | 2/1987 | Reid .............................. 435/240.23 |
| 4,673,649 | 6/1987 | Ham et al. . |

OTHER PUBLICATIONS

Woodley, D. T. et al., *Abstracts Amer. Soc. Cell Bio. and Amer. Soc. Biochem. Mol. Bio.* 4536, (Jan. 29–Feb. 2, 1989).
Gabriels, J. E. et al., *The Toxicologist*, Abstract of the 28th Annual Meeting, Society of Toxicology 1:1038, (Feb., Mar. 1989).
Barrandon, T. and H. Green, *Cell* 50:1131–1137, (1987).
Madison, K. C. et al., *J. Invest. Dermatology* 90:110–116, (1988).
Bernstam, L. I. et al., *In Vitro Cell. Devel. Bio.* 22:695–704, (1986).
Boyce, S. T. et al., *J. Biomed. Materials Res.*, 22:939–957, (1988).
Chamson, A., et al., *J. Cell Bio.* 95:2123, (1982).
Neutral Red Bioassay, Catalog #CC-0500, Clonetics, San Diego, Calif.
Kondo, S. et al., *J. Invest. Dermatology*, 72:85–87, (1979).

*Primary Examiner*—Sam Rosen
*Attorney, Agent, or Firm*—Hamilton, Brook, Smith & Reynolds

[57] ABSTRACT

A method is described for producing tissue from cells, such as keratinocyte, epithelial or endothelial cells, in virto. Cells are grown on a porous cell-growth substrate having specific growth factors therein e.g., on a collagen activated coated microporous substrate. Cells can be grown to form a confluent monolayer or differentiated tissue which can be used for studying cell toxicology.

15 Claims, 4 Drawing Sheets

METHOD FOR GROWING CELLULAR TISSUE

BACKGROUND OF THE ART

A number of methods for culturing mammalian cells of different tissue origins have been reported. However, many of these cells are difficult to grow in vitro and, when grown, are not morphologically similar to in vivo tissue.

Green and Rheinwald (U S. Pat. No 4.016,036, 1977) describe a procedure for serially cultivating keratinocyte cells grown in the presence of mitotically inhibited fibroblasts. Without a second cell type (e.g.. 3T3 fibroblasts), the keratinocyte cultures were neither uniform nor differentiated. A major disadvantage of using tissue produced by this method for in vitro toxicology and other studies is the presence of fibroblasts. Although the fibroblasts are mitotically inhibited, they are still metabolically active. As such, the metabolic activity and/or cellular components of the fibroblasts interfere with assays for cells under study.

Woodley and co-workers (Joint Meeting of *Amer. Chem. Soc. Cell. Biol.* and *Amer. Soc. Biochem. Mol. Biol.*, Abstract 4536, page 798a, Jan. 29–Feb. 2, 1989. San Francisco, Calif.) describe a method for growing keratinocyte cells on collagen without the use of a second cell type. A medium containing epidermal growth factor and bovine pituitary extract was employed to facilitate cell growth. Epidermal tissue grown by this method, however, cannot be raised to the air/liquid interface since there is no means for providing nutrition to the tissue.

A method for growing keratinocyte cells at the air/liquid interface has been described by Bernstam, I. L. et al., *In Vitro Cell Dev. Biol.* 22:695-704 (1986). Cells grown on a collagen substrate produced confluent monolayers; however, non-uniform areas of stratification were observed.

Thus, it would be desirable to produce a tissue which is morphologically similar to its in vivo conterpart for in vitro toxicology and other studies (for example, transepidermal drug transport).

SUMMARY OF THE INVENTION

This invention pertains to methods for producing tissue, in vitro, and to a substrate for growing tissue thereon. Specifically tissue from cells is prepared by contacting a porous cell-growth substrate with cell culture medium comprising growth factor specific for growth of cells of interest, such as keratinocyte cells, epithelial cells and endothelial cells. Growth factor is then contacted with the substrate under conditions whereby it is dispersed within or onto the substrate. Preferably, the cell-growth substrate comprises a microporous membrane which is coated with cell-growth supporting material such as collagen. Cells are subsequently seeded onto the cell-growth substrate whereby the cells contact or are in close proximity to the growth factors to form a cell culture. The seeded cell-growth substrate is maintained under conditions suitable for cell growth to thereby produce tissue. Tissue produced by the methods of this invention can be a confluent monolayer of cells or it can be a differentiated, multilayer of cells. Various stages of tissue growth, from the formation of a confluent monolayer and through the stage of stratification and terminal differentiation, can be achieved by manipulating the conditions for cell growth. The culture can be grown submerged in culture medium or it can be raised to the air/liquid interface to mimic in vivo conditions. In either case, the cells form tissue which is evenly distributed over the substrate, uniformly stratified, and terminally differentiated. Tissue produced by the methods of this invention is sufficiently morphologically similar to its in vivo counterpart so that it is useful for in vitro toxicology.

This invention also pertains to a method for determining toxic effects of a substance on tissue produced by the methods of this invention and to toxicological kits comprising the tissue grown on a cell-growth substrate having growth factors thereon. Alternatively, the kit will comprise the cell-growth substrate and cells of interest for growing on the substrate.

DETAILED DESCRIPTION OF THE INVENTION

Figure 1:
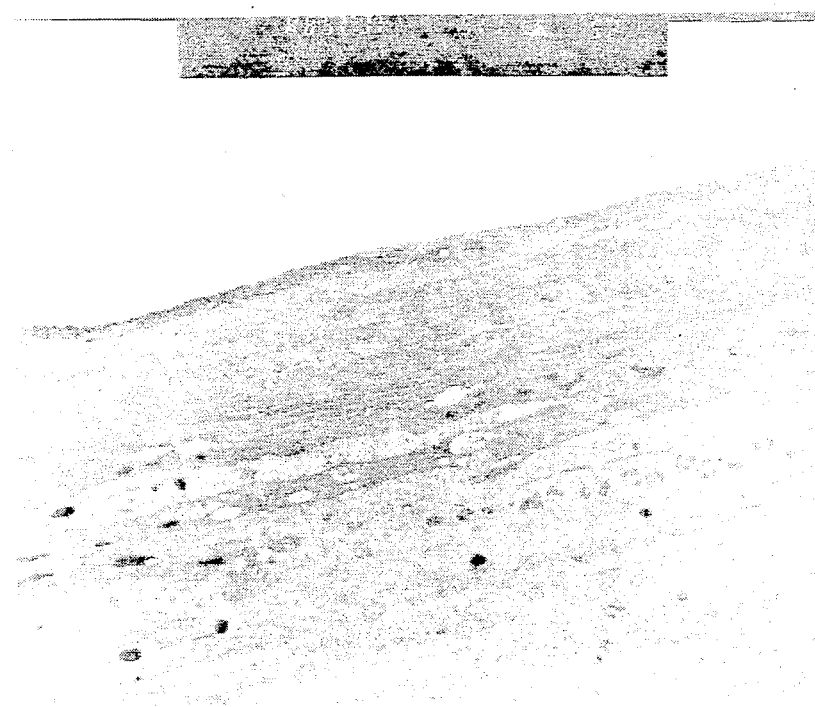
FIG. 1 is a transmission electron micrograph (TEM) which shows the air/liquid interface of a keratinocyte sheet with cornified envelopes grown according to the methods of this invention.

Cells which are suitable for producing tissue by the methods of this invention, include but are not limited to, keratinocyte cells, hepatocyte cells, nerve cells, endothelial cells, and epithelial cells of any tissue origin such as, corneal epithelial and pulmonary epithelial cells. The cells can be from any natural tissue source (mammalian or other cell source), or they can be genetically engineered. The term "tissue" is herein intended to mean an organization of cells grown to form a confluent uniform monolayer or multilayer tissue that can be stratified and terminally differentiated.

The cell-growth substrate is critical to the proliferation and differentiation of cells to form tissue similar to in vivo tissue. A porous cell-growth substrate is defined herein to be any substrate which will support cell growth. Suitable cell-growth substrates will have a porous structure which can facilitate diffusion of nutrients to the cells, particularly to the basal cells of the tissue. For example, the porous cell-growth substrate can contact medium and supply tissue raised to the air/liquid interface with sufficient nutrients. The cell-growth substrate can be any porous natural or synthetic polymer, such as collagen, cellulosic membranes, polycarbonate, polytetrafluoroethylene, nylon membranes and nylon mesh. Other porous materials which can be used as a cell-growth substrate are glass filters and ceramics. Preferably, the cell-growth substrate comprises a microporous membrane. One particularly suitable support is Millicell-CM ™ microporous insert (Millipore Corporation, Bedford, Mass.). In addition to membranes, filters can be used and are included within the scope of the invention. In a preferred embodiment, the cell-growth substrate is coated with a cell-growth supporting material, such as collagen, laminin or fibronectin.

The surface of the porous cell-growth substrate must be favorable for cell growth. In particular, a cell growth substrate will support growth because: its natural properties are sufficient; or it is treated to provide cell growth properties; or it is coated with a cell-growth supporting material, such as collagen. The surface of the substrate is then activated to provide sites for attachment of growth factors.

In one embodiment, porous cell-growth substrate can be treated (chemically or non-chemically) to provide activated sites for attaching growth factors to the cell-growth substrate. The method by which a cell-growth substrate is treated to provide activated sites for adherence of growth factors depends upon the substrate. A growth factor is any molecule which facilitates growth of cells of interest, such as cell-specific growth factors (for example, epidermal growth factor) hormones, cell culture medium, peptides, carbohydrates and glycoproteins.

In another embodiment, the cell-growth substrate is coated with a cell-growth supporting material which is treated for attaching growth factors thereto. Suitable cell-growth supporting materials are proteinaceous materials such as collagen, gelatin, laminin and fibronectin. When the cell-growth substrate is coated with collagen, the collagen can be chemically treated by crosslinking it with gluteraldehyde or other crosslinking agents to provide activated sites for attaching the growth factors thereto. Non-chemical methods, such as exposure to radiation, can be used to activate sites on the substrate.

A cell-growth substrate having activated attachment sites can then be contacted with cell culture medium comprising growth factor specific for cells of interest, under conditions whereby the growth factor is dispersed within the substrate. The cell culture medium can contain one type of growth factor or it may contain a number of different types of growth factors which are specific for cells of interest. The growth factors can be dispersed throughout the substrate or they can be dispersed to areas of the substrate which will actually contact the cells, such as the surface of the cell-growth substrate. When the substrate is coated with crosslinked collagen, it is believed that the growth factors chemically attach themselves (e.g., by covalent attachment) to the activated sites located on the collagen. However, other means of attaching growth factors to the substrate are embraced by this invention.

To insure that all activated sites on the substrate have been inactivated or neutralized (i.e., all activated sites have been bound with a growth factor), the cell culture medium is removed from the substrate and an additional amount of medium comprising growth factors and non-specific protein is contacted with the substrate to saturate remaining activated sites. This step quenches or deactivates the substrate and insures a substantially uniform distribution of growth factors within the substrate. Preferably, the non-specific protein is serum or albumin which can bind to remaining activated sites.

After the surface of the cell-growth substrate has been prepared, cells of interest are seeded onto the substrate whereby the cells are contacted with the growth factors to form a cell culture. The seeded cell-growth substrate is then maintained under conditions suitable for cell growth to produce monolayer sheets of tissue. Further cell growth will result in multilayered tissue which is differentiated. After the cells have grown for several days, the culture can be raised to the air/liquid interface where the cells can further differentiate to yield tissue similar to its in vivo counterpart. Alternatively, the cells can be maintained as a submerged culture. Tissue grown by the methods of this invention can be subsequently removed from the substrate and harvested.

In the preferred embodiment, tissue from keratinocyte cells can be produced by providing a porous cell-growth substrate, such as microporous membrane, having a layer of collagen coated thereon. The collagen is treated (for example, by crosslinking it with gluteraldehyde) to provide activated sites for attaching growth factors thereto. The treated collagen-coated substrate is then contacted with cell culture medium comprising epidermal growth factor and pituitary extract which comprises growth factors therein, under conditions whereby the growth factors are dispersed within the substrate and can be chemically attached thereto. Cell culture medium for proliferation of normal human epidermal keratinocytes (NHEK) containing epidermal growth factor and bovine pituitary extract had been described by Boyce and Ham (U.S. Pat. No. 4,673,649, June 16, 1987) and modified by Clonetics, Inc. (San Diego, Calif.), as Keratinocyte Growth Medium.

The cell culture medium is then removed from the substrate. The resulting medium-free substrate is contacted with additional medium which is modified with serum and calcium. The amount of medium added is that which is sufficient to saturate remaining activated sites with growth factor and/or serum to thereby deactivate or quench the substrate. Once the substrate has been deactivated, keratinocyte cells are seeded onto the substrate to form a cell culture. The cell seeding density can be from about $1 \times 10^2$ cells/cm$^2$ to about $1 \times 10^7$ cells/cm$^2$. Preferably, keratinocyte cells are seeded at a seeding density of $1 \times 10^5$ cell/cm$^2$ to $8 \times 10^5$ cells/cm$^2$. The culture is maintained under conditions suitable for keratinocyte cell growth to thereby produce tissue containing keratinocyte cells. Tissue raised to the air/liquid interface will be stratified, terminally differentiated epidermis.

Toxicological effects of drugs, chemicals and cosmetics on mammalian cells is currently evaluated, in vivo. For example, toxicity of cosmetics is tested using the Draize eye irritancy test on rabbits. As a result of such tests, there is increasing public awareness and criticism of the use of animals for toxicity testing. In response to public concern, many countries have banned the use of animals for toxicology. Thus, alternative methods for screening toxic effects of drugs and chemicals must be developed.

Toxic effects of substance, such as drugs, chemicals and cosmetics, can be evaluated using tissue produced by the methods of this invention. A substance to be evaluated is administered to tissue (from cells at any stage of growth and differentiation) grown on a cell-growth substrate, as previously described. Cellular response to the substance is observed. The response can be a change in cell morphology or it can be one or more chemical changes in the cell. The response is then evaluated to determine toxic effects of the substance, For example a substance to be screened for its toxic effects can be topically applied to stratified, terminally differentiated epidermis. Toxicity of the substance can then be assessed.

Additionally, since tissue produced by the methods of this invention sufficiently, morphologically resemble in vivo tissue, it can be used in other physiological and clinical applications, such as to study cellular development into tissue, pharmacological mechanisms and transdermal transport of drugs. The tissue can also be used as a tissue replacement for wounds, burns and the like.

A kit for in vitro toxicology will comprise a porous cell-growth substrate having growth factors specific for growing cells of interest dispersed therein; tissue from cells of interest grown on the substrate; and reagents for determining the toxicity of a substance. Preferably, the substrate will be a crosslinked collagen gel coated on a microporous cell-growth substrate and the cells are keratinocyte cells which are grown to produce terminally differentiated tissue. The tissue, however, can be readily available at various stages of cell growth from a monolayer to a stratified, multilayer tissue.

In another embodiment, the above kit can comprise a suspension of cells which can be seeded onto the cell-growth substrate and grown to thereby produce tissue at any desired stage of cell growth. The cell-growth substrate minus the cells can be sold freeze-dried or frozen. The kit can further comprise one or more reagents for determining toxicity of a substance. Preferably, the cell-growth substrate is a microporous polymeric membrane and the cells are keratinocyte cells.

The invention will be further illustrated by the following examples.

EXAMPLE 1

Keratinocyte Growth on a Collagen-Coated Cell-Growth Substrate.

Preparation of a Collagen-Coated Cell-Growth Substrate

Two parts by volume of collagen from rat tail Type I, about 3 mg/ml (Collaborative Research, Lexington, Mass.), was diluted with one part 70% ethanol and mixed well by vortex. The resulting solution was sterile and could be stored refrigerated prior to use.

MilliCell-CM TM porous substrate inserts (Millipore Corporation, Bedford, Mass.) were placed in 100 mm petri dishes. 50 $\mu$l and 500 $\mu$l of the collagen/ethanol mixture were added to petri dishes containing 12 mm and 30 mm Millicell-CM TM inserts, respectively. Five or six drops of concentrated ammonium hydroxide were placed around the periphery of the petri dishes. The petri dishes were then covered and incubated for 45 minutes at room temperature to allow the collagen to gel.

The resulting collagen gel or gels were washed one time with 70% ethanol. The Millicell-CM TM inserts containing the collagen gel were immersed in 70% ethanol and incubated at room temperature for one hour to dehydrate the gel. The resulting gel was contracted on the Millicell-CM TM insert to form a dense gel. The gel was rinsed one time with sterile water and then washed three times by aspirating the inserts with sterile phosphate buffered saline (PBS).

Crosslinking the Collagen

A 25% aqueous solution of gluteraldehyde was diluted 1:10 in PBS to yield a concentration of 2.5% gluteraldehyde in PBS. The resulting solution was filtered to remove particulates. PBS was removed from the Millicell-CM TM inserts described in the previous section. The inserts were then immersed in sterile 2.5% gluteraldehyde solution and incubated for one hour to activate the surface of the collagen and crosslink it. The resulting crosslinked gel was washed three times with sterile PBS.

Attachment of Growth Factors to Gluteraldehyde Activated Collagen-Coated Substrate PBS was removed from the crosslinked collagen gels as prepared in the previous section The crosslinked collagen gel was then immersed for 1.5 hours in modified MCDB 153 nutrient medium (Keratinocyte Growth Medium (KGM), Clonetics, Inc., San Diego, Calif.; U.S. Pat. No. 4,673,649, Boyce, S. and R. Ham). The medium contained Epidermal Growth Factor (EGF) and Bovine Pituitary Extract (BPE).

After 1.5 hours the medium was removed and replaced with a modified KGM solution. The KGM solution was modified by adding 10% Fetal Bovine Serum (FBS) and 1 5 mM calcium chloride from 200 mM stock solution of tissue culture grade calcium chloride in water. The collagen gel was then immersed in the modified KGM solution for one hour to quench any remaining active sites on the crosslinked collagen gel.

Seeding the Cell-Growth Substrate

Normal human epidermal keratinocytes (NHEK) were acquired as secondary passaged cell strains from Clonetics, Inc. The secondary cultures were fed daily with serum-free KGM and were used to seed crosslinked collagen gels, prepared as described above, when the cultures were between 60-80% confluent. The KGM medium of the seed culture was replaced with fresh KGM medium prior to seeding the collagen gel.

The keratinocytes were released from the culture flask with trypsin/EDTA (ethylenediaminetetraacetic acid) and prepared as a single cell suspension in modified KGM (10% FBS, 1.5 mM calcium). The cells were then seeded on the collagen gel substrate at a keratinocyte seeding density of $3-6 \times 10^5$ cells/cm$^2$.

Growth of Geratinocytes on the Cell-Growth Substrate

The seeded collagen gel substrate was incubated at 37° C. The culture was maintained as a submerged culture and was replenished daily with fresh solution of modified KGM (10% FBS. 1.5 mM calcium).

The keratinocyte cells attached to the collagen substrate within 24 hours. The submerged culture of cells grew to a confluent monolayer and began to stratify between days 4-8. The cultures also exhibited a significant electrical resistance between days 4-8, of about 150-200 ohms cm$^2$, which indicated that the keratinocyte cell sheet was uniform and coherent. The cultures were raised to the air/liquid interface between days 4-8 for further differentiation and keratinization of the culture.

Figure 2:
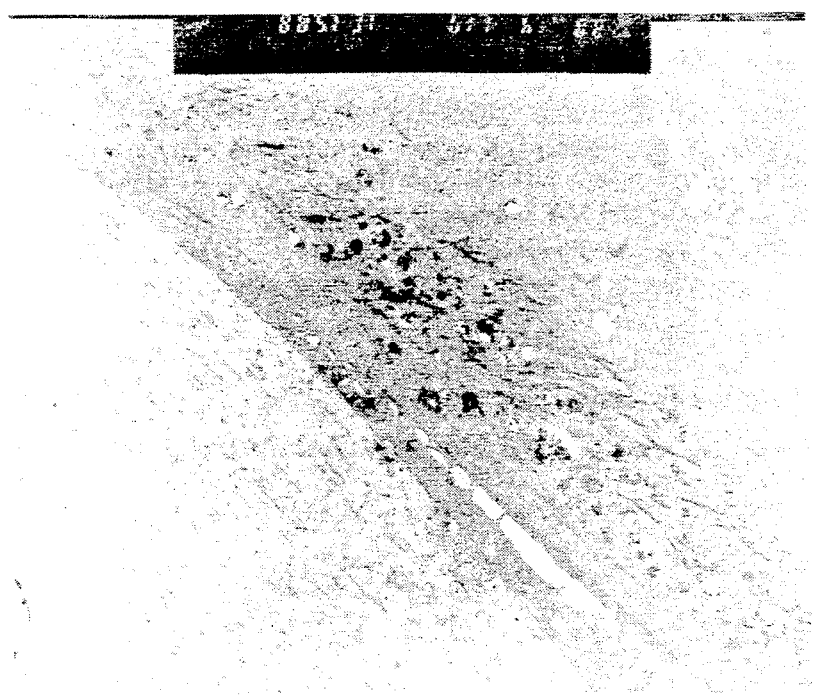
FIG. 2 is a TEM which shows the basal portion of the keratinocyte sheet shown in FIG. 1.

FIGS. 1 and 2 are transmission electron micrographs of a keratinocyte sheet raised to the air/liquid interface for 14 days. The micrographs show a stratified, terminally differentiated sheet of keratinocyte cells (i.e., epidermis). At the air/liquid interface, the sheet has cornified envelopes which are characteristic of human epidermis, in vivo. Cells which are several layers down from the air/liquid interface contain keratinohyalin granules (dense, black intracellular bodies). There are also numerous desmosomal junctions. In the basal portion of the sheet (FIG. 2) at the collagen gel interface, there is a smooth basal membrane. Inside the basal membrane are numerous keratin filaments and mitochondria.

Directly beneath the basal membrane is a black line which ultrastructurally appears to be the formation of a basement membrane.

Figure 3:
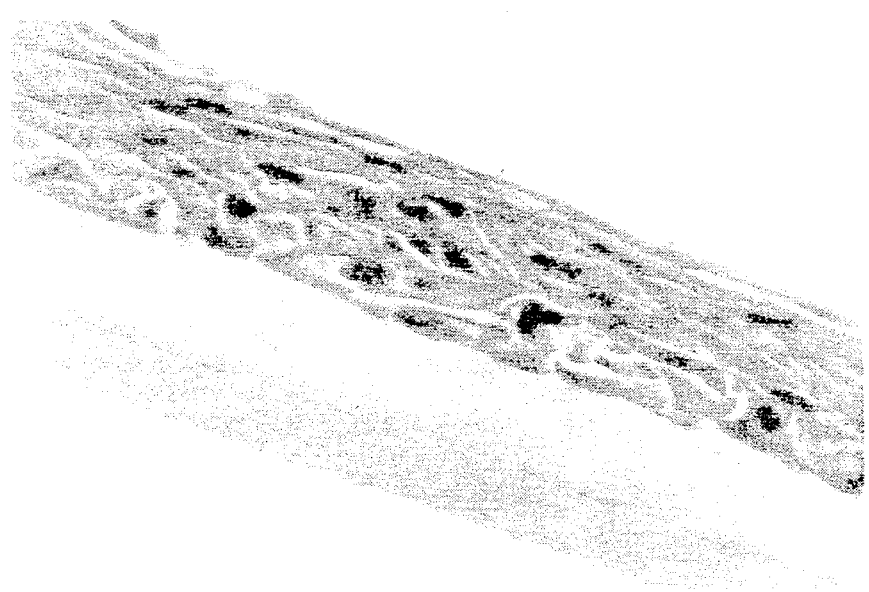
FIG. 3 shows a hematoxylin and eosin stained histological cross-section of a uniform sheet of keratinocytes grown on a modified, crosslinked collagen-coated cell-growth substrate made according to this invention.

FIG. 3 shows a hematoxylin and eosin stained histological cross-section of a uniform sheet of keratinocytes grown on the crosslinked collagen-coated cell-growth substrate (Millicell-CM TM microporous membrane) as described above. Note that the layer of keratinocyte cells and collagen are of uniform thickness. In a similar experiment, (results not shown), keratinocyte cells were grown on an unmodified, uncrosslinked collagen-coated cell-growth substrate (Millicell-CM TM microporous membrane). A histological cross-section of substrate showed a disorganized mass of keratinocyte cells. In addition, the collagen under the cell mass appeared to be thinning, which may indicate collagenase degradation.

EXAMPLE 2

In Vitro Toxicological Study.

Cell Culture

Madin-Darby Canine Kidney cells (MDCK, ATCC No. 34) were cultured in Dulbecco's Modified Eagle's Medium (DMEM) with 10% FBS. Normal human epidermal keratinocytes (NHEK) (Clonetics, Inc., San Diego, Calif.) were cultured in KGM with 10% FBS and 1.7 mM calcium. Both cell types were grown on collagen-coated microporous Millicell-CM TM culture plate inserts with Biopore TM membranes (Millipore Corporation, Bedford, Mass.). The collagen-coated microporous membranes were prepared as described in Example 1. Both cell types were seeded at $5 \times 10^5$ cells/cm$^2$.

MDCK and NHEK cells grown on the collagen-coated membranes exhibited a differentiated in vivo-like ultrastructure characterized by cuboidal morphology, basal nucleus, desmosomes and tight junctions (in MDCK cells) and stratification (in NHEK cells). MDCK cells were used for cytotoxicity studies at confluence, 4 days after seeding. NHEK cells were used for similar studies at 8 days after seeding.

Cell Staining

Rhodamine 123 (a mitochondrial stain) was diluted in Earle's Balanced Salt Solution (EBSS, 10 μg/ml). Both cell types were stained for 1 hour with the rhodamine solution at room temperature. Cells were washed prior to cytotoxicity testing.

BCECF-AM (an analog of 6-carboxyfluorescein diacetate and an intracellularly fluorescent stain of viable cells; Molecular Probes, Inc., Eugene, Oreg.) was diluted in serum-free, phenol red-free Dulbecco's Modified Eagle Medium (DMEM) (40 μg/ml) and used to stain both cell types for 35 minutes at room temperature. Cells were rinsed prior to cytotoxicity testing.

Cytotoxicity Testing and Detection

Dilutions (0-100 μM) of either mercuric chloride or cadmium chloride in EBSS were applied only to the apical membrane surface. In similar experiments, dilutions of either 10% Sodium dodecyl sulfate (SDS) or Tween 20 (Sigma Chemical, St. Louis, Mo.) in DMEM were applied only to the apical membrane surface.

Dye release as an indicator of cytotoxicity was measured using a Fluoroskan II Spectrofluorimeter (Flow Labs, Inc., McLean, Va.). Supernatant containing released fluorescent dye was read directly using an excitation wavelength of 485 nm and an emission wavelength of 538 nm.

Cytotoxicity Results

The dose response efflux of the fluorescent probes, such as rhodamine 123 and carboxyfluorescein diacetate analogs, was measured by quantitifying fluorescence released to the apical compartment. The efflux was indicative of the degree of mitochondrial toxicity and cell membrane damage in response to heavy metals (i.e., mercuric chloride or cadmium chloride) and detergents (i.e., SDS or Tween).

With rhodamine 123 probes, mitochondrial toxicity preceded disruption of plasma membrane integrity. Using fluorescent probes of BCECF-AM, acute apical plasma membrane damage was observed by release of fluorescence to the apical compartment. Extensive membrane damage is indicated by release of fluorescence to both the apical and basal compartments.

For 10% SDS, assay sensitivity extended to dilutions of 1 in 10.000.

Figure 4:
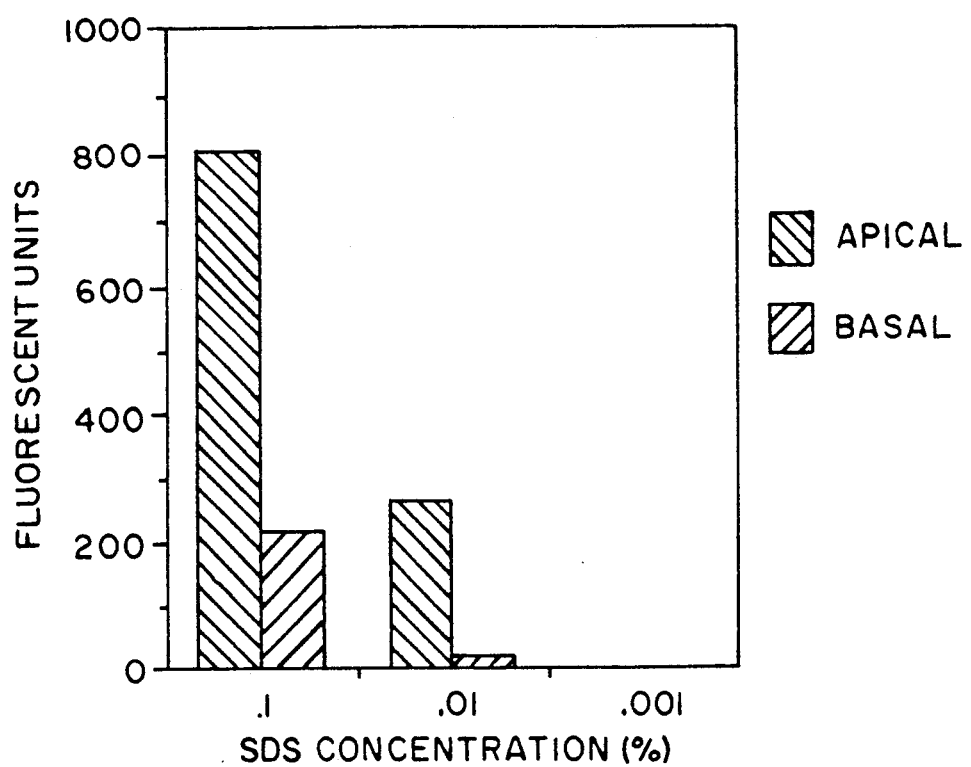
FIG. 4 shows a dose-response curve for keratinocyte cells grown on a collagen-coated microporous cell-growth substrate according to the methods of the invention and exposed to various concentrations of sodium dodecyl sulfate (SDS).

FIG. 4 shows the dose response curve for the apical and basal membrane of keratinocyte cells exposed to various concentrations of SDS. Keratinocyte sheets were grown on collagen-coated microporous membranes and were stained with fluorescent dye C-1354 an analog of carboxyfluorescein (Molecular Probes, Inc., Eugene, Oreg.). Damage to the cell was assessed by measuring the fluorescence in both the apical and basal compartments.

Equivalents

Those skilled in the art will recognize, or be able to ascertain using no more than routine experimentation, many equivalents to the specific embodiments of the invention described herein. These and all other equivalents are intended to be encompassed by the following claims.

I claim:
1. A method of producing tissue from keratinocyte cells, comprising the steps of:
  a. contacting a collagen coated polymeric microporous substrate suitable for growing cells with growth factor specific for growth of said keratinocyte cells in vitro, wherein the collagen comprises activated sites for attaching the growth factors thereto;
  b. subsequently seeding keratinocyte cells onto the microporous substrate; and
  c. maintaining the seeded microporous substrate under conditions suitable for cell growth to thereby produce a confluent monolayer of tissue or uniformly differentiated multilayer tissue.

2. The method of claim 1, wherein tissue grown on the microporous substrate is maintained as a submerged culture or raised to the air liquid interface.

3. Tissue produced by the method of claim 1.

4. A method of producing tissue from keratinocyte cells, comprising the steps of:
  a. treating collagen coated on a polymeric microporous substrate suitable for growing cells, to thereby provide activated sites in the collagen for attaching growth factors thereto;
  b. contacting the collagen-coated microporous substrate with cell culture medium comprising epidermal growth factor and pituitary extract containing growth factor therein, under conditions whereby the growth factors are dispersed within the substrate and attached thereto;

c. removing the medium from the substrate to provide a medium-free substrate;

d. contacting the medium-free microporous substrate with a sufficient amount of cell culture medium comprising serum, epidermal growth factor and pituitary extract containing growth factor therein, to saturate remaining activated sites;

e. subsequently seeding keratinocyte cells onto the microporous substrate; and f. maintaining the seeded microporous substrate under conditions suitable for cell growth to thereby produce a confluent monolayer of tissue or uniformly differentiated multilayer tissue.

5. A method of preparing a substrate for growing tissue from one cell type thereon, comprising the steps of:

a. treating a collagen coated polymeric microporous substrate to thereby provide activated sites in the collagen for attaching growth factor thereto;

b. contacting the collagen coated microporous substrate with cell culture medium comprising growth factor specific for growth of said cells under conditions whereby the growth factor is dispersed within the substrate and attached thereto;

c. removing the medium from the substrate to provide a medium-free substrate; and d. contacting the medium-free substrate with an amount of cell culture medium comprising growth factor and non-specific protein sufficient to saturate remaining activated sites, to thereby produce a substrate for growing a confluent monolayer of tissue or uniformly differentiated multilayer tissue thereon.

6. The method of claim 5 wherein the microporous polymeric substrate is a microporous membrane.

7. A substrate for growing tissue from cells produced by the method of claim 5.

8. A method of producing tissue from one cell type in vitro, comprising the steps of:

(a) treating a collagen coated porous substrate suitable for growing cells, to thereby provide activated sites in the collagen for attaching growth factor thereto;

(b) contacting the collagen coated porous substrate with growth factor specific for growth of said cells in vitro whereby the growth factor is dispersed within the substrate and attached thereto;

(c) subsequently seeding the cells onto the porous substrate; and (d) maintaining the seeded porous substrate under conditions suitable for cell growth to thereby produce a confluent monolayer of tissue or uniformly differentiated multilayer tissue.

9. The method of claim 8 wherein the porous substrate is a microporous polymeric membrane.

10. Tissue produced by the method of claim 8.

11. The method of claim 8, wherein tissue grown on the porous substrate is maintained as a submerged culture or raised to the air liquid interface.

12. A method of producing tissue from one cell type in vitro, comprising the steps of:

a. treating a collagen coated porous substrate suitable for growing cells to thereby provide activated sites in the collagen for attaching growth factor thereto;

b. contacting the collagen coated porous substrate with cell culture medium comprising growth factor specific for growth of said cells under conditions whereby the growth factor is dispersed within the substrate and attached thereto;

c. removing the medium from the substrate to provide a medium-free substrate;

d. contacting the medium-free substrate with an amount of cell culture medium comprising growth factor and non-specific protein, sufficient to saturate remaining activated sites;

e. subsequently seeding the cells onto the porous substrate; and f. maintaining the seeded porous substrate under conditions suitable for cell growth to thereby produce a confluent monolayer of tissue or uniformly differentiated multilayer tissue.

13. The method of claim 12 wherein the porous substrate is a microporous polymeric membrane.

14. The method of claim 12 wherein the cells are keratinocyte cells.

15. Tissue produced by the method of claim 12.

* * * * *